United States Patent [19]

Rosenblatt

[11] Patent Number: 5,071,648
[45] Date of Patent: Dec. 10, 1991

[54] POLYMERIC BROAD-SPECTRUM ANTIMICROBIAL MATERIALS

[75] Inventor: Solomon Rosenblatt, Noank, Conn.
[73] Assignee: Merocel Corporation, Mystic, Conn.
[21] Appl. No.: 500,918
[22] Filed: Mar. 29, 1990

Related U.S. Application Data

[62] Division of Ser. No. 334,037, Apr. 6, 1989, abandoned.
[51] Int. Cl.⁵ .................. A61K 31/765; A61K 31/18; A61L 15/03; A61F 13/00
[52] U.S. Cl. .................. 424/78.06; 424/445; 424/431; 424/411; 424/423; 424/667; 424/78.26; 523/122; 521/82; 525/61
[58] Field of Search .................. 424/81, 82, 667, 660, 424/444–447, 78

[56] References Cited

U.S. PATENT DOCUMENTS

| | | | |
|---|---|---|---|
| 1,867,222 | 7/1932 | Karns | 128/849 |
| 2,381,621 | 8/1942 | Schmelkes | 574/150 |
| 3,328,259 | 6/1967 | Anderson | 424/445 |
| 4,031,209 | 6/1977 | Krezanoski | 424/660 |
| 4,128,633 | 12/1978 | Lorenz | 424/667 |
| 4,255,415 | 3/1981 | Chrai et al. | 424/78 |
| 4,323,557 | 4/1982 | Rosso et al. | 424/448 |
| 4,340,043 | 7/1982 | Seymour | 128/849 |
| 4,396,642 | 8/1983 | Bolt et al. | 427/54.1 |
| 4,552,138 | 11/1985 | Hofeditz et al. | 424/445 |
| 4,675,009 | 6/1987 | Hymes et al. | 604/304 |

FOREIGN PATENT DOCUMENTS 0174108 9/1985 European Pat. Off. .

OTHER PUBLICATIONS

CA 108:38846s, Bogomolnyi et al., "Iodine-Containing Films Based on Vinyl Alcohol (Co) Polymers", (1987).
CA 106:157217f, Oishi et al., "Formation of Poly(vinyl Alcohol)-Iodine Complex in Water Swollen Films", (1987).
CA 104:225596q, Oishi et al., "Effects of the Degree of Hydration of Swollen Poly(vinyl Alcohol) Films on their Iodine Complexes", (1986).
CA 68:43119s, Mokharach, "Iodinated High Polymers and their Application in Medicine and Veterinary Science" (1967).
CA 68:50501p, Savko et al., "Absorption Spectra of Poly(vinyl Alcohol) Films Colored in Solutions in Iodides and Bromides" (1967).
CA 109:120443n, Gribov et al., "Nature of the Conducting Properties of Polymeric-Film Detectors Based on Polyvinyl . . . " (1988).

Primary Examiner—Thurman K. Page
Assistant Examiner—E. J. Webman
Attorney, Agent, or Firm—Ostrolenk, Faber, Gerb & Soffen

[57] ABSTRACT

A sustained and controlled release form of iodine is achieved by a complex of polyvinyl alcohol and the iodine characterized by a low water solubility. The polyvinyl alcohol may be reacted to form hydroxylated polyvinyl acetal sponge and the sponge is topically applied as an antimicrobial agent which releases controlled amounts of iodine sufficient to kill germ cells with minimal toxicity to surrounding tissue.

11 Claims, No Drawings

POLYMERIC BROAD-SPECTRUM ANTIMICROBIAL MATERIALS

This is a divisional of application Ser. No. 07/334,037, filed Apr. 6, 1989; now abandoned.

TABLE OF CONTENTS

I. Background of the Invention
   A. Field of the Invention
   Background Art
II. Objects and Summary of the Invention
III. Detailed Description of the Preferred Embodiments
IV. Examples
   A. Post-Treatment of Films (Complexing after Formation)
      Examples 1–4
   B. Pre-Treatment of Films (Complexing of PVA with Iodine before Formation into a Film)
      Examples 5–9
   C. Bactericidal Matrix Coating
      Examples 10–13
   D. Post-Treatment of Open-Cell Foam
      Example 14
      Methods 14(A)–14(H)
      Results
   E. In Situ Complexing of PVA Sponge During Formation
      Examples 15–17
   F. Increased Activity with Surfactants
   G. Increased Activity with Altered pH
   Adhesive Dressings
V. Results of Testing Complexed PVA Systems
VI. Microbicidal Properties of High Density PVA/I Complexed Foam Containing Approximately 10% Iodine Based on Weight of Merodine Sponge
VII. Products Contemplated

BACKGROUND OF THE INVENTION

A. Field of Invention

This is a divisional of application Ser. No. 07/334,037, filed Apr. 6, 1989; now abandoned.

This invention relates to polymeric sheets, coatings, sponges and gels, and more particularly, complexes of insolubilized PVA and PVA by itself with iodine and/or borates that exhibit antiseptic, broad-spectrum antimicrobial activity in a controlled and sustained manner.

B. Background Art

Numerous potential pathogens may be present on the skin and exposed tissue. It is desirable for the growth of disease-producing microorganisms to be inhibited and preferably for these microorganisms to be destroyed so as to control patient infection and encourage wound healing. As a result, the application to the skin or tissue of topical bactericidally active agents has become a standard part of the aseptic technique for wound care.

Iodine is an outstanding microbicide, with an extraordinary range of action. Part of its mode of action is that it is able to penetrate the cell walls of microorganisms rapidly, and block certain essential hydrogen-bonding in amino acids. Also, it has a powerful, oxidizing effect on S-H, -S-S- groups, which are essential factors in protein production. It is effective against a wide range of microorganisms, including bacteria, tubercle bacilli (Mycobacteria), fungi, protozoa, lipid and medium viruses, as well as non-lipid and small viruses. Iodine is designated as an intermediate germicide only because spores are not readily killed with weak concentrations. However, iodine has the greatest degerming efficiency compared to the other halogens, chlorine and bromine, since it is deactivated by proteins at least three times slower than chlorine and four times slower than bromine Therefore, under normal conditions of use where there is the presence of large amounts of dissolved proteins as in blood, serum, or sputum, iodine would not be rendered ineffective. Iodine has the additional advantage that its disinfecting properties are independent of the pH value of its environment. Therefore, unlike chlorine, for example, iodine would not be rendered ineffective in an acid pH. It would likewise not be deactivated quickly in an alkaline pH.

Low concentrations of iodine react relatively slowly as compared with proteins in general and therefore it remain available to react with bacteria to which it generally has a greater affinity. It is in this way that iodine can exhibit its unique advantageous selectivity towards microorganisms while maintaining a very low level of cytotoxicity to the host cells. However, because of iodine's physical and inherent chemical properties, its use as an antiseptic, broad-spectrum antimicrobial has been limited because state of the art delivery methods allows for the liberation of too much free iodine which can be toxic to living cells.

Elemental iodine, in the form of Tincture of Iodine (alcoholic solution), is highly toxic if brought into contact with the body cavity. It causes swelling and bleeding of the mucous membranes. Iodine is therefore generally not impregnated into bandages because of the potential for this corrosive destruction of the skin. A 1% Tincture of Iodine solution can release in excess of 10,000 PPM of iodine into the surrounding tissue environment all at once, when only 0.2 PPM of iodine may be required to be antimicrobially effective. Consumption by an adult of 30 grams of Tincture of Iodine can be fatal. Also, elemental iodine is volatile having a high, intrinsic vapor pressure which causes, over time, a loss in germicidal potency. This occurs when the iodine content volatizes from coated surfaces or from antiseptic preparations, especially when exposed to the environment at elevated temperatures.

Borates, although not as microbially active as iodine, have antimicrobial properties. In combination with iodine, they enhance its activity. Elemental boron by itself, however, is considered toxic to internal tissue.

One example of an attempt to preserve or tame the outstanding antimicrobial activity of iodine, while simultaneously reducing its corrosive toxic and vapor pressure properties, is a two-part dressing, using an iodide salt in one component and an oxidizer in the other, which react on moisture contact, liberating iodine, as in U.S. Pat. No. 1,867,222. Another example is the use of water soluble complexes of polyvinyl pyrrolidone iodine complex (PVP/I) as disclosed in U.S. Pat. No 4,128,633. The latter is illustrative of a complex of iodine and an organic carrier commonly known as an iodophor. This complexing of iodine "harnesses" the iodine, thereby controlling its rate of release. The former describes a delayed release mechanism for free iodine. However, both these aqueous solution complexes still have limited application in spite of their slower release properties, as their water miscibility with body fluids still causes excess delivery and quick dissipation of the released iodine, resulting in possible cytotoxicity and loss of long time effectiveness.

Iodophors are loose complexes of elemental iodine or triodide, solubilizers, and a polymeric carrier that serves, not only to increase the solubility of the iodine, but also to tame the iodine to provide a sustained release reservoir for the iodine. The carriers, heretofore, have been neutral, water soluble polymers, with mainly polyvinyl pyrrolidones as the principal commercialized polymer. Polyether glycols, polyacrylic acids, polyamides, polyoxyalkylenes, starches and polyvinyl alcohol also form iodophors. Carriers may also exhibit varying degrees of surface active properties that improve the penetration or wetting characteristics of the solution in use. Upon dilution, these iodophor complexes form micellar aggregates, which are dispersed, upon dilution, with water or bodily fluids, and the iodine linkage to the polymer is progressively weakened until the iodine can be regarded as free to generate antimicrobial concentrations. These iodine complexes in aqueous solution have the advantage over pure, elemental iodine solutions, in that because they are present in far less concentration they greatly reduce irritation to tissue, unpleasant odor, staining of tissue and corrosion of metal surfaces such as surgical instruments, but dissipate relatively quickly because of their miscibility and reaction with body fluids.

Generally, when such a complex is in equilibrium with the aqueous phase, and then diluted, the solution will have increased availability of free iodine within a given fixed volume. These iodophors, because of their water solubility, therefore tend to dissipate their antimicrobial action quickly, because as a solution, they are water miscible with fluids throughout the wound site, and react relatively quickly with serous fluids while reacting with the bacteria. The concentrations of iodine in water-based systems can be much higher than what is required for its antimicrobial intent, and iodine is dissipated by side reactions with body fluids, resulting in the iodine reservoir being prematurely used up and thus allowing recolonization of the wound site.

Compared to Tincture of Iodine, the improved release properties of PVP/I iodophors have resulted in the greater use of iodine in preoperative skin preps, surgical scrubs, washes, douches, lotions and ointments. However, their limited iodine reserves and dilution factors have meant that such iodophors are effective for a given disinfecting purpose for a limited time only. Microorganisms that have survived the initial application, because of limited longevity of the antimicrobial agent, may act as a seed to cause the pathogen population to rise again to its initial level.

Most water miscible broad-spectrum antimicrobials exhibit this deficiency. Continuous application of the antimicrobial agent to the site is therefore required, to inhibit the increase in population. For example, sustained release can be provided, with prolonged antibacterial activity under a plastic, self-adhering surgical drape film. U.S. Pat. No. 4,323,557 describes a process for incorporating N-Vinyl-Pyrrolidone (NVP) in the polymeric backbone of a pressure-sensitive adhesive of which the pyrrolidone component serves to complex and slowly release the iodine. The iodophor-based adhesive film provides a sterile operative surface, and acts as a barrier to isolate the incision from contaminating skin flora. This product is for use as an incisible self-adhering drape and is not intended for wound healing dressings or wound packings.

A major disadvantage of PVP/I complexes is that their safe and efficacious antimicrobial action is limited to use on skin or, in some cases, on intact mucosa. This is because their water solubility, as mentioned above, results in excess releases of free iodine when introduced into the wound site. Considering that as little as 0.2 PPM of iodine is sufficient to kill enteric bacteria (10 minutes at 25° C.), and under the same conditions, 3.5 PPM and 14.6 PPM of iodine, respectively, are sufficient to kill amoebic cysts and enteric viruses, PVP/I complex solutions can instantaneously introduce thousands of excess parts of available iodine in one bolus (i.e., an uncontrolled burst of solution), dependent upon the site. Large concentrations of free iodine, as with borates, are cytotoxic and cytopathic to healthy tissue, and can have an adverse affect of reducing the body's natural defense mechanism against infection. A paper published in the British Journal of Surgery, 1986:73:95, stated "topical Povidone-Iodine not recommended for application on post appendectomy wounds." The paper was based on the results obtained from the appendicular fossa during the operations, and was predictive of the patients' likelihood to develop wound infection. In patients who had mixed aerobic and anaerobic culture results, 20% developed sepsis when PVP/I was used, and 7% when systemic antibodies alone were used.

PVP/I solutions are administered to open wound sites, as in burns, even though they are toxic, when stopping infection takes precedence over proper wound healing. Typical commercial antibacterials such as soap, Hexachlorophene, Hibiscrub, alcohol and Chlorhexidine are all water soluble and water miscible preparations which exhibit various efficacious antimicrobial properties on the skin, but all are relatively toxic upon contact with living cells.

OBJECTS AND SUMMARY OF THE INVENTION

It is the central object of this invention to overcome the deficiencies of the foregoing antimicrobial solutions, by forming complexes which are less water miscible than those previously known, wherein iodine and borate, either individually or in combination, are complexed with polymeric, biocompatible materials which are less water soluble, to form antimicrobial iodophors that will release the iodine and/or borate at a slow rate over an extended period of time.

It is a further object of this invention to form these less soluble complexes with vehicles such as films, gels and sponge foams, that exhibit a combination of superior physical properties such as high absorption of body fluids, strength, softness and hydrophilicity. Such vehicles, furthermore, should not leave residues or fibers behind, should be biocompatible, and should not, by themselves, support the growth of microorganisms. The iodine should not wash out of the complexes, but should remain active. Furthermore, these polymer systems should act as an iodine reservoir and hydrophilic bridge to the tissue for the transfer of controlled amounts of iodine, as in the transdermal drug delivery device, disclosed in U.S. Pat. No. 4,675,009.

It is another object of this invention to polymerize soluble PVA to form insoluble acetals in the form of foams, sheets or gels, and subsequently form less soluble iodine complexes with these acetals with solutions of iodine, iodides, borates or their combinations.

It is yet another object of this invention to form more insoluble antimicrobial polymeric iodophors. Such iodophors are provided by forming insoluble polymeric complexes of acetalized PVA and iodine or borate or combinations thereof.

These and other objectives are achieved by providing a complex of polyvinyl alcohol and iodine which has a low solubility such that it releases iodine in the a sustained and a controlled manner in an amount which will kill germ cells but not damage living tissue. An antimicrobial borate material may also be complexed with the polyvinyl alcohol. The complex may be with PVA or PVA acetal film, sponge, foam or gel and used as a wound dressing. The iodine is preferably complexed with hydroxylated polyvinyl acetal sponge and topically used. Additionally, the complex may be combined with a matrix, such as cloth or non-woven material.

DETAILED DESCRIPTION OF THE PREFERRED EMBODIMENTS

The prior art has not foreseen the use of polyvinyl alcohol solid state complexes of iodine or borates to effect iodine delivery control, for a wound healing device or other topical antimicrobial device. Controlled release iodine/borate soluble polymeric complexes are known and found to be effective and safe, when used topically on the skin and on internal tissue. These PVA/iodine complex antimicrobial solutions also have been found to function as an adjunct to systemic antibiotics by focusing a sustained kill and inhibiting future microbial action at the infected or potentially infected site.

Less soluble, iodine complexed, high polymer foams, sheets and the like from PVA copolymers also do not contaminate the wound site by leaving behind healing inhibiting foreign materials, such as lint particles from gauze, or petroleum ointment jelly vehicles, to contain topical antibiotics. The non-biocompatibility of petroleum-based ointments is, for example, reported in a paper on myospherulosis by David H. Chait, M.D., "An Iatrogenic Disease," Boys Town Natl. Inst. for Communication Disorders in Children, Omaha, Nebraska, circa 1985. Complications from gauze particulate matter left behind in the operation site is reported by the Federal Drug Administration. See Federal Register 22856 (June 24, 1988).

Complexes of iodine or borates, with polyvinyl alcohol derived films, sponges, foams or gels, either by themselves or acetalized (PVA/I complexes), are remarkably superior, to currently available iodine delivery systems since these systems form even less soluble complexes of iodine that provide an enormous reservoir of available iodine for antimicrobial effectiveness (approximately 20,000 to more than 100,000 PPM) because it is slowly released, thereby maintaining a constant degerming effect on the environment. These high level iodine reserves are enormous, considering that as little as 0.2 PPM iodine is sufficient to kill enteric bacteria (10 minutes at 25° C.)

These complexes are distinguished from the prior art solutions by being free of water to a degree such that the total weight of water within the complexed material, or in contact with the complexed material, is less than the total weight of the complex.

These PVA/I complexes, like PVP/I, do not have the disadvantages of elemental iodine, such as unpleasant odor, irritation and deep staining of tissue, and corrosion of metal surfaces The PVA/I complexes also have the distinct advantage of having superior sustained and controlled antimicrobial effectiveness, as compared to current iodophors.

A further object of this invention is to achieve a less soluble iodophor by finding a suitable polymer or precursor monomer that complexes with iodine, either before or after the polymerization, and yields a relatively insoluble complex which is solid.

Moreover, PVA/I forms less soluble iodine complexes, releasing iodine only when there is a significant amount of organic matter, or when microbes are present. If the PVA solid complex is placed in an aliquot of saline only, iodine is released. However, the iodine forms an equilibrium with the saline with no loss of iodine from the system. As organic matter is added to the saline which contains the solid complex, then some iodine is released, anywhere from as little as a few PPM to about 100 PPM. This represents only about 1/100th the amount of iodine released by 1% Tincture of Iodine. As iodine is released, it is taken up by microbes forming an irreversible chemical reaction, killing the microbes. As released iodine is taken up, only then is more released, until equilibrium is maintained. A great reservoir of iodine is complexed in the PVA system, and because of its very limited solubility, is not readily released to side reactions causing rapid iodine depletion and resulting loss of effectiveness common to other iodophors. However, even though PVA/I complexes are relatively insoluble, the complex releases the iodine in controlled amounts that are relatively constant, to its surrounding liquid medium over long periods of time, even at a maximum challenge to the system. PVP/I has been reported to have a reservoir of available iodine of about 10,000 PPM, of which only up to 35 PPM is available immediately. PVA/I complexes, on the other hand, provide a reservoir of available iodine of 20,000 to more than 100,000 PPM, with controlled sustained release properties superior to the current iodophors, resulting in the least harm to host cells.

Commercial solutions of PVP/I contain only 1% iodine, and approximately 9% PVP polymer or 10% iodine by weight based on the polymer PVA/I complexes, on the other hand, are easily prepared with up to 20% iodine by weight, based on the polymer. In addition, 100% of the polymer complex is in contact with the surface, giving greater effectiveness, as compared to the diluted PVP/I solution.

TABLE

Available vs. Free Iodine

A. Non-complexed Iodine
   LIQUID (water)
   1) Iodine in water (poorly soluble - saturates at 0.03%)
      Available = 0.03%     Free = 300 ppm
      Reservoir = 0
   2) Tincture of iodine (alcohol/water) = (1%)
      Available = 1%        Free = 10,000 ppm
      Reservoir = 0

B. Complexed Iodine
   LIQUID (water)
   1) 10% Povidone - Iodine (Betadine)
      Available = 1%        Free = 1 to 35 ppm
      Reservoir = 10,000 ppm
      (1% = 10,000 ppm)
   SOLID (air/water)
   1) PVA (acetalized)/iodine
      Available = 2-5%      Free = 0 to 70-100 ppm
      Reservoir = 20,000 to
      >100,000 ppm Also, the PVA/I based, less soluble complexes have a unique intrinsic colorimetric indicator which reveals when iodine content is depleted. As iodine depletion occurs, the polymer begins to turn from blue/black, which is the color of the complex, to lighter shades of blue or purple and eventually completely white, indicating that the iodine is depleted and the dressing should be changed.

The colorless polymer may be recomplexed and returned to the blue/black color in situ, by replenishing the sponge or sheet with fresh I/KI. However, care must be taken to never add more iodine than the sponge can complex, thereby causing a potential toxic excess of iodine to the wound site. When all the iodine is complexed from the I/KI solution by the PVA sponge the typical elemental reddish color of the solution changes to water clear, or slightly greenish. On the other hand, if excess iodine is present it is easily known as it will be indicated when the reddish color of the solution runs out of the polymer when the sponge is squeezed. Free iodine can be rinsed out of the sponge with pure water until an equilibrium of about 10 PPM of iodine is reached with the rinse water. Free iodine may be more quickly removed by controlled treatment with a reducing agent, e.g., dilute sulphite solutions.

Polyvinyl alcohol was reported to give a characteristic blue color with iodine in aqueous solutions indicating the forming of an iodine complex. With PVA containing acetate groups, the color is more reddish. 20% acetate groups give the maximum color intensity. The blue color disappears when the solution is heated above 50° C., and in all other respects, is similar to starch in this behavior. (Polyvinyl Alcohol Polymer Monographs-Basic Properties and Uses, Vol. 4, pp.74–75, notes 84–86 to article by J. G. Pritchard.)

Polyvinyl alcohol is an active molecule suitable for polymerizations, and, by itself, is considered to be a biocompatible material. It is well known that the blue starch (amylose) iodine complex is a strong antimicrobial and is comparatively stable. In contact with tissue, it continues active for much longer than iodine itself, and if the iodine content is approximately one percent, it is devoid of tissue irritant reaction. However, polymers of starch that have high enough tensile strength, elongation, and other physical characteristics that are desirable for bandage material, are more difficult to make than polymers based on polyvinyl alcohol (PVA) systems.

It is known that injectable solutions of PVA gels containing PVA/Iodine complex have strong fungicidal properties and their bactericidal properties are enhanced by the inclusion of boric acid. Hence, solutions of the double complex, wherein a molecule of PVA complexes with both iodine and boric acid, have been used as injectables in the treatment of infections in animals. For example, a gel prepared from 125 grams of PVA, 2.5 grams of iodine, 10 grams of potassium iodide, 2 grams of Congo red and 5 grams of boric acid made up to a liter, can be injected into the tissues of animals, and maintains active microbial properties for several days. Russian Journal, S. N. Ushakov, Dokady Akad, Navk SSSR, 134 643. (Polyvinyl Alcohol Polymer Monograph, J. G. Pritchard, Volume 4, Chapter 6, p. 123, Reference #78.) However, these water soluble complexed solutions are not suitable for dressings, and will release more iodine or borate than is necessary for killing the microorganisms because of their water solubility with the excess iodine or borate, possibly causing cytotoxicity. Also, the solutions, per se, do not have the physical integrity to be used as a dressing, packing or drape.

PVA water soluble resins react with iodine similarly to water miscible starches, and starch iodine complexes are known to be antimicrobial but have poor mechanical properties. Also, starch, per se, has the intrinsic disadvantage of forming adhesions and granulomas in the body, as reported in the literature with starch coated surgical gloves. In view of the foregoing, it was decided to determine if iodine complexes could be made of PVA systems and have suitable mechanical properties.

A number of PVA polymers with desirable physical and mechanical properties were synthesized and subsequently complexed with iodine. It was found that formalized, preferably medium molecular weight fully hydrolyzed polyvinyl alcohol in the form of cellular materials, or formalized or unformalized sheets, gels or coatings of PVA complexed with iodine, produce relatively insoluble iodophors with excellent antimicrobial properties and controlled, sustained release properties over an extended time. One example of a formalized PVA polymer is an open celled foam, as described in U.S. Pat. No. 4,098,728. This foam or open celled sponge was subsequently complexed with iodine to illustrate the characteristics of formalized PVA foam iodine complexes.

Any other formalized PVA foam such as those previously described, for example, in U.S. Pat. No(s). 2,609,347, 3,663,470 and 3,737,398, may be similarly complexed with iodine. Examples are given below. Other foam examples which were iodine complexed in-situ or during polymerization are also given below.

Further examples of formalized and unformalized PVA gels and coatings, complexed with iodine either pre- or post-formation, are given below.

The iodine in these complexes may be derived preferably from potassium iodide solubilized iodine. PVP/Iodine complexes are also sources of iodine for PVA/I complex, as the PVA/I complex is more stable and reacts with the iodine from the PVP. Sublimed iodine whose vapor reacts with the PVA, chloroform solutions, and tinctures, are examples of other sources of iodine.

The elucidation of the structure of the formalized or unformalized polyvinyl alcohol iodine complex presents an interesting, though perplexing problem. Potassium iodide in solution seems to be preferable to facilitate the formation of the complex, and this suggests that $I_3$-ions may be involved in the mechanism of formation of the complex. On the other hand, the formation of the iodide ions may be merely to solubilize, and therefore increase, the concentrations of the available iodine. It may be that iodine molecules are adsorbed, end to end, at the existing microcrystalline sites that form in the hydrated polymer, or that the iodine molecules cause an additional helical crystallization of the PVA chains, in which iodine molecules are enclosed, end to end in close association. This is almost identical with the behavior in the starch (amylose)-iodine complex, the structure of which is fairly well understood. However, the blue color of both the starch and PVA disappears when their solutions are heated above 50° C., while the formalized PVA iodine complex is stable until 100° C., which is the point at which the iodine is being driven off in the form of elemental iodine due to its vapor pressure. When allowed to cool, the resultant characteristic orange iodine colored solution is recomplexed with the formalized PVA polymer, to reform the characteristic blue/black color. This gives further credence to the theory that the iodine is absorbed at the microcrystalline sites as these sites would be reformed upon cooling of the solution with the reaggregation of the molecules to reform the complex at the sites and the characteristic blue/black color.

It appears that the formalization of the PVA and then post-formation iodine complexing results in increased stabilization of the system, with reduced volatility of the iodine, and tendency to less freely release more iodine than is needed. The blue complex appears more chemically stable than the PVP/I reddish complex, since it holds onto the iodine more firmly and only releases controlled amounts. Since only as little as 0.2 PPM may be required for bactericidal effectiveness, while still preserving the health of host cells over a prolonged period, increasing the stability of the iodine complex is desirable. Microorganisms are more sensitive to iodine than healthy cells; therefore keeping the free iodine concentration low enough, creates a selectivity towards the killing of microorganisms. When boric acid is present in this formalized PVA-iodine-KI system, it catalyzes the complex reaction, causing it to form more quickly. For example, when a 2% solution of iodine in 4% potassium iodide is saturated with boric acid and then the formalized PVA open cell foam is submerged in the solution, a clear solution area forms at the interface between the orange iodine solution and the polymer, indicating extraordinary affinity of the polymer for the iodine. Without the boric acid this does not occur. This borate-iodine formalized PVA system exhibits no worse antimicrobial properties than without the borate and in some cases gives improved activity. However, the stability of the complex, as indicated by its complex reaction rate, may further improve stability and, therefore, longevity of antimicrobial action.

Boric acid complexes with PVA, in much the same way it does with sugars and other polyhydroxylic compounds. At pH values above 8, two of the acid hydrogen ions react with a pair of alternate hydroxyl groups forming a cyclic ortho ester yielding 2 moles of water. The third hydrogen, when base-catalyzed, cross-links with a hydroxyl group on another chain, causing gel points, cross-linking and relative insolubility. However, the reaction is reversible and the boric acid/PVA complex, which is relatively insoluble when heated to 150° F. in water, will dissolve with excess water and heat beyond 150° F.

When boric acid is present in the aqueous PVA/I-KI systems to produce these additional gel points and cross-linking, further stabilization of the iodine complex is achieved, with benefits as described previously, and in addition, the complexed borate ion, in some cases, adds antimicrobial effectiveness, as demonstrated by the culture experiments reported below.

EXAMPLES

The following are examples of processes of two general types: in which relatively soluble films, described above are initially formed and then complexed with iodine and/or borate (referred to as post-treatment); or in which the PVA resin component is initially complexed with iodine and/or borate, previous to film formation or polymerization (referred to as pre-treatment).

Post-treatment of films (Complexing after formation)

The following examples illustrate the formation of prepolymerized, and highly insoluble films or cellular foam to be subsequently iodine complexed. The formulae presented are only examples of many formulations that will achieve various physical properties, such as rate of cure or crosslinking, to achieve insolubility. Varying the molecular weight generally yields higher strength materials, proportionately to increase in molecular weight. Varying aldehyde content gives greater water insolubility and stiffness with increased content. Varying acid content gives faster cures proportional to content.

1. A 7.5% solution of medium molecular weight PVA of a predetermined amount dependent on the final desired film thickness, is cast on a flat surface, and the water is allowed to evaporate. The resultant film is submerged in a 2% solution of iodine in 10% potassium iodide until the film darkens and does not gain any more weight. The complexed film is washed and dried. This film can be dissolved in 180° F. water.

2. A solution of medium molecular weight PVA is cast as in Example #1, and the resultant film is submerged in a saturated boric acid solution at 25° C. Then the pH of the boric acid solution is adjusted with sodium bicarbonate to pH 10. The film is kept submerged in the pH 10 solution until it does not gain any more weight and the film is washed and dried. The film can also then be complexed with iodine as in Example #1. The film can be dissolved in 180° F. water.

3. The film is cast as in Example #1, and the resultant film is submerged in a solution of 2% iodine in 10% potassium iodide and saturated at 25° C. with boric acid. The film is submerged in the solution until there is no more weight gain. The dark film is washed and dried. This film will dissolve in 180° F. water.

4. A process for achieving a highly insolubilized film is to cast the film as in Example #1, and after drying, submerge in a mix of 80 cc of 50% sulphuric acid and 58cc of 37% formaldehyde for about 16 hours at 110° F., or until the film no longer dissolves in boiling water. Afterwards, the film then can be complexed with iodine as in Example 1. The iodine complexing can occur either before or after curing.

Pre-Treatment of Films (Complexing before formation)

The following examples disclose films that are made by first complexing the PVA before casting:

5. 300 grams of a 12% solution of medium molecular weight PVA was mixed with 800 cc of 50% sulphuric acid at 100° F. To the mix was added 580 cc of 37% formaldehyde and mixed until homogenous. The film was cast as per Example #1, and allowed to cure at room temperature. The film was washed in water and neutralized in 10% sodium bicarbonate solution, and washed to pH 7 and dried. The insolubilized films are complexed as per the above Examples 1 to 3. These films will not dissolve in boiling water.

6. To 100 cc of 7.5% solution of medium molecular weight PVA, slowly add 1.5 grams of potassium iodide and mix until fully dissolved. Then add 1.5 grams of iodine and mix until iodine is fully dissolved, cast, dry, and wash, to remove salts and air dry film. This film will not dissolve at 180° F.

7. To 100 cc of 7.5% solution of low molecular weight PVA, slowly add boric acid solution and mix until fully dissolved. Cast film, dry, and treat in a sodium bicarbonate solution adjusted to pH 9 for 30 minutes. Remove soluble salts by washing and dry film. This film will not dissolve at 180° F.

8. To 100 cc of a 7.5% solution of low molecular weight PVA, slowly add 1.5 grams of potassium iodide, 1 gram of iodine, and 15 grams of boric acid. Mix into the resin each ingredient thoroughly before next addition is made. Cast, dry, wash to remove soluble salts and dry film. This film will dissolve at 180° F.

The choice of complexing before casting, or complexing after film formation, may depend on ease of processing. Viscosity or gels may develop in the PVA solution, depending upon temperature and/or rate of addition of complexing agents. Steps may have to be taken to use shear mixers, increased dilutions, higher temperatures and deaeration steps to achieve easy processable casting solutions. Post-complexing (complexing after formation of the film) requires additional steps and time to effect good complex concentrations, plus extended washing times.

9. In addition to batch casting, films may be extruded or continuously cast on a heated drum. To achieve various degrees of softness, gel formation or plasticizing of films or foams, polyhydroxylic compound may be substituted for portions of the water in the PVA solution. Examples of these plasticizers are 2.2 Diethyl 1.3 propanediol, glycerol, 1.4 pentanediol, propylene glycols, ethylene glycols, etc.

Bactericidal Matrix Coating

To achieve extra film strength or reinforcement, the filming solution may be coated onto a matrix, such as a piece of cloth or nonwoven webbing, either to entirely encapsulate the matrix, or to form a light coat, to act as a sizing agent. These bactericidal complexes would be useful for surgical drapes, gowns, and dressings. The bactericidal gels may be useful for wet dressings and for burns.

Examples of a bactericidal gel, limp films or web-reinforced gel matrixes are the following:

In Examples 1 to 3 described above under "Post-Treatment of Films," the water content of the PVA solution may be substituted by a polyhydroxylic compound, or the final water content of the film may be increased by limiting drying time to act as a plasticizer.

10. 10.0 grams of medium molecular weight PVA is dissolved in 45 grams of water containing 1.5 grams of pentanediol by mixing at 180° F. with constant stirring until complete dissolution. After the resin solution cools, the film is cast and allowed to dry at 125° F. overnight. The film is then immersed in a 2% iodine solution dissolved in 4% potassium iodide until the characteristic blue/black color is achieved and there is no more weight gain. The film is washed of all free iodine and air-dried. The resultant film is limp and conformable and its complexed iodine is typically antimicrobial.

11. The resin solution of Example 10 is poured into a coating trough and a dacron mesh with 1 mm openings is submerged and impregnated with the resin solution and allowed to dry at 125° F. overnight. The impregnated mesh is then complexed with iodine solution as in Example 10.

12. As per Example 1, only 60% of the water is evaporated. The soft, limp, gel-like film is supported on a polyethylene sheet while drying and being complexed with the iodine. The final, soft, moist film is hermetically packed to preserve its water content.

13. The resin solution of Example 12 is poured into a coating trough, and a 2 mil thick non-woven dacron web is submerged and impregnated with the resin solution and allowed to dry until only 60% of the water is evaporated. The soft gel-impregnated web is complexed with iodine in the usual manner and hermetically packed as in Example 12.

Post-treatment of open-cell foam

The following is an example of an open cellular foam which is complexed after formation:

14. This example illustrates a method for forming the surgical sponge component of this invention to be subsequently complexed with iodine, having a uniformly medium pore size between 0.3 and about 1.0 mm. Into a rotary beater was mixed 475 grams of a medium molecular weight fully hydrolyzed polyvinyl alcohol with 4050 grams of deionized cold water which was mixed until a smooth paste was achieved. The temperature of the paste then was raised to 180° F. and mixing was effected for about 5 minutes at this temperature. The mixture was then cooled to 110-120° F. and 15 grams of Triton X-100 wetting agent was added and the resultant mixture was agitated for 5 minutes. 700 cc of 50% sulphuric acid at a temperature of 110° F. was added to the mixture so that its volume was 9800 cc. Thereafter, 500 cc of 37% aqueous formaldehyde solution at 100-110° F. was added slowly to the mixture and was agitated for 60 seconds. The temperature of the mix was about 105 to 108° F. and the volume was about 12,600 cc. The beaters were then rotated in a reverse direction for 1 minute at 1/6 the original speed until the observed time of larger bubbles in the froth ceased. Reverse mixing was continued until the mix became noticeably thicker. This froth then was extruded into a plastic mold that had been previously heated to 120° F. The froth was cured in the mold for 1 hour at 140° F. and the mold was then removed from the oven and cured at room temperature for 20 hours. Thereafter, the mold was opened and the sponge obtained was washed by alternately running it through reionized water and rubber rolls until the rinse water had a pH of 3 minimum. The damp sponge was cooled until frozen solid and then cut to desired shape. The sponge slices were then defrosted and final washed until 50 cc of the wash water, upon vigorous shaking, did not produce a foam which maintained itself longer than 10 seconds. The sponge pieces were then placed between layers of open cell foam pads, and dried while held between the pads to maintain shape and flatness of the sponge. Drying was achieved by initial case hardening at 160° F. for 1-2 hours and then holding at 110-120° F. in a dehumidified chamber for one day or until the sponge was completely dry. The sponge maintained by this procedure had uniformly sized medium pores within the range of between about 0.3 and about 1.0 mm as determined by a scale built into the eyepiece of a stereoscopic microscope.

The sponge had a liquid-holding capacity of 22-25 times its own weight as determined by ASTM D-1117-74 5.1.2 and an absorbency rate of less than 10 seconds as determined by ASTM D-1117-74 5.2.

The foam was then immersed in a 2% iodine solution dissolved in 4% potassium iodide at room temperature. The characteristic blue/black complex began to form. The sponge was palpated into the iodine solution to effect complex formation in all the interstitial spaces throughout the open cell sponge matrix. Iodine uptake from less than 1% of the sponge weight to more than 15% of sponge weight was achieved depending on sponge density (amount of sponge solids) and time for the complex reaction to take place.

Iodine Post-Formation-Complexing Process - For PVA Sponge

Methods 14(A) to 14(H) which follow are only illustrative of various combinations in the post-complexing of PVA sponge with iodine.

The complexing process uses a bath of iodine, for example, iodine (2%) and Potassium iodide (4%). The bath is prepared by mixing dry iodine crystals with granular potassium iodide before adding to the water (grinding in a mortar and pestle is helpful but not essential).

Approximately one quarter of the water is added to the dry components and agitated until all solids are dissolved (usually within 10 minutes). The remainder of the water is added and mixed well, approximately two minutes.

The bath is designated MD 2/4, indicating the iodine/potassium iodide concentration.

All examples of complexing the PVA foam with iodine have been based on the MD 2/4 ratio, but other variations are possible.

Where treatments have required lowered concentrations, the volume of MD 2/4 is noted by the addition of water.

Three sponge types have been used in the experiment.
CF150 high density sponge - 4 mm thick (3.5–4.5 lbs./ft$^3$)
CF90 intermediate density - 6 mm thick (2.5–3.5 lbs./ft$^3$)
CF50 low density - 15 mm thick (1.5–2.5 lbs./ft$^3$)

Several variations of treatment were utilized which used combinations of I/KI with high and intermediate density sponge with chemical rinses and with water only.

Final treatment of sponge with wetting agents was examined. Additives of boric acid and acetic acid were included.

All samples were dried at 105–115° F. in a circulating air oven.

EXAMPLES

Method 14(A)

A sample of high density sponge (CF150, 4 mm thick) weighing 16 grams was saturated in 200 cc of MD 2/4 solution for 3 minutes.

The sponge was rinsed with squeezing between rinses until no more than 10 PPM of free, uncomplexed iodine is detectable in the wash water.

An iodide rinse (0.5% KI) was used before an additional 10 water rinses.

The sponge was dried at 105–115° F. for 16 hours (overnight) in air.

Individual weighed samples of this method indicated total iodine uptake to be 9.8 to 10.2% by weight of sponge.

Method 14(B)

To determine iodine concentration vs. complexing rate and uptake, samples of sponge (CF 150, 4 mm thick) were treated in MD 2/4 solution (12 cc/gram of sponge) the volume of the iodine solution was diluted with water to 4 times the normal volume. This method provides the same total iodine per gram of sponge in a greater volume of solution. The sponge is saturated with a lower initial iodine content but continues to absorb the iodine since reaction time is increased to 10 minutes. The sponge was rinsed as in Method 14(A).

Iodine uptake increased to a range of 12.8 to 15.8% in six samples, indicating that diluting the iodine does not decrease uptake assuming enough time is allowed.

Method 14(C)

A sample of both CF150 (4 mm thick) high density sponge was treated with MD 2/4 solution at the normal saturation level of 12 cc/gram. The sponge was allowed to absorb the iodine for 20 minutes.

The rinsing (without squeezing) was done in cascading water until pale amber drippings indicated minimal residual free iodine.

A sodium sulfite (less than 1%) solution rinse for 10 seconds followed.

Rinsing was continued in water for 5 minutes until no more than 10 PPM of free iodine could be detected in the rinse water.

The sponge was dried at 105–115° F.

CF150 iodine (weight gain) =11.4%. The use of relatively inexpensive sulfite in place of potassium iodide did not affect the uptake of iodine.

Method 14 (C-a)

A sample of CF90 (6 mm thick) intermediate density sponge was treated as in method 14(C) with a total of 550 ml MD 2/4+100 ml H$_2$O.

Weight gain increased to 20.4%.

The use of higher levels of available iodine raise the total content (by weight) of the complex but result in higher rinse loss of iodine. Quantitative determinations of iodine uptake into the sponge indicate that within limits of 1–25%, the sponge will absorb 50–60% of the iodine available from the solution.

Method 14(D)

(Sponge was not treated with wetting agent)

Samples of CF150 (4 mm thick) were soaked overnight (16 hours) in MD 2/4 at the rate of 10.4 cc/gram of sponge.

These samples were rinsed as in Method C and dried. Weight gain=8.8% of iodine.

The conclusion is that the absence of wetting agent has a slight effect on the wetting of the sponge pore surfaces, but is not significant.

Method 14(E)

Samples of CF90 were treated in bath of 150 cc MD 2/4 and 50 cc water. The stand time was increased to 40 hours.

A cascading water rinse was used without any chemical.

After drying at 105–115° F. These samples indicated a weight gain of 17.5% of iodine.

Method 14(F)

Samples of CF50 (15 mm thick) were treated at the rate of 12 cc/gram in MD 2/4 50 cc with 150 cc water added. This saturation volume allowed total absorption of the iodine as evidenced in pale green effluent after 4 hours.

No water rinse was necessary. A final single rinse in 5% glycerol was used to increase wetting properties.

Weight gain=3.6% when treated a second time with 300 ml MD 2/4+100 ml H$_2$O weight gain increased to 21.2%. The conclusion is the small initial iodine uptake does not "passivate" the sponge pores and additional iodine when available will be absorbed.

Method 14(G) - (Bactericidal Samples for Borate Testing)

Samples CF90 (6 mm thick) were treated in 100 cc MD 2/4 which had 5% boric acid and diluted with 100 cc water. The saturation volume of 12 cc/gram was maintained.

Cascading water rinse was used with drying at 105-115° F. overnight (16 hours).

Method 14(H)

Samples of CF50 (15 mm thick) were treated in MD 2/4 50 cc with 10 cc glacial acetic acid and 140 cc water added. Acetic acid treatment demonstrates that pH of the final system may be influenced to be more effective in pH sensitive microbial environments.

The sponge was soaked for 5 minutes then squeezed and rinsed in 5% glycerol and then squeezed and dried 5 hours at 105-115° F.

The purpose was to provide an acetic acid residue to lower the pH of the sponge when rewetted during use. When wetted, and the pH measured was reduced to 4.0 from the normal pH of 6.5.

Results

Preliminary results have shown no overt impedance of phagocytic activity caused by the PVA/I complexed sponge material that occurs in the presence of polymorphonucleated leukocytes (P.M.N.)/staph aureus test systems.

Unsterilized PVA/I complex was shown to be chemically sterile.

Upon exposure to 2.5 megarads beta radiation which sterilized the PVA/I complex and then comparing its antimicrobial activity to the unsterilized material, no change in antimicrobial activity was evident. Upon exposure to the environment in an office and manufacturing area without protection, for a one year period, no change in antimicrobial activity was evident. Upon submersion under saline in a closed test tube for a one year period, no change in antimicrobial activity was evident.

In situ complexing of PVA Sponge during formation

The PVA foam may also be complexed in situ during formation and polymerization of the sponge. The following are three examples illustrative of how this can be accomplished, but other variations are possible.

EXAMPLE 15

The desired iodine content based on final sponge or solids weight is calculated and a 2% solution of this amount of iodine in 4% potassium is made up. Some of the water normally used during the sponge polymerization may be utilized in making up the iodine solution. The iodine solution is added to the acidified resin but before the aldehyde addition. All additions are slow with vigorous mixing. The resin resolution is frothed, cast, cured and washed in the normal manner.

EXAMPLE 16

The aldehyde and iodine solution is premixed and the combination is added to the acidified resin mix with slow, vigorous mixing, and frothed, cast, cured and washed in the normal manner.

EXAMPLE 17

After the resin mix is acidified, frothed and having received the aldehyde, the iodine solution is added slowly with vigorous mixing. The iodized mix is cast, cured and washed in the normal manner.

In Examples 15-17, the iodine is precipitated at first as elemental iodine firmly suspended in the resin medium giving a characteristic orange-red color to the pre-polymer. When the aldehyde begins to react to form the acetal, the iodine also slowly begins to complex, giving the characteristic blue/black color to the foam. Converting the elemental free iodine to the complexed form is achieved by the time the foam is fully polymerized. The time for curing varies with cure temperature.

A specific example is Example 18 described below:

EXAMPLE 18

Step A.

100 gm of PVA (15% solids) solution is added to 20 gm of sulfuric acid (50%) and mixed well.

Step B.

50 gm of formaldehyde (37% in methanol) is mixed with 25 gm of MD 2/4 (2% $I_2$ in KI).

Step C.

Solution B is combined with solution A and mixed completely. The solution is characteristically orange changing to the blue/violet color of the complex within 5-10 minutes.

Increased Activity with Surfactants

In some instances, there may be a special need to kill bacteria more quickly. This can be because of limited contact time with the PVA/I complex, the presence of a massive infection, or a strong likelihood that a massive infection will result. A wipe for decontaminating instruments exposed to the AIDS virus is an example of a limited contact occurrence, and a gunshot or shrapnel wound is an example of a potential massive infection.

It has been found that surfactants, when incorporated into the interstitial spaces of the sponge, accelerate the activity of the iodine, resulting in faster kills. It is not fully understood if there are other synergies, besides the generally known penetration properties of surfactants, which may allow for this faster iodine transfer.

The following experiment illustrates the increase of activity:

Conditions

PVA sponge used was medium density, designated as CF90, complexed to contain approximately 10% iodine based on weight of the sponge. $\frac{1}{4}"\times\frac{1}{4}"\times 2"$ sponge pieces were wet out with 10 cc of 1% saline containing 10% wetting agent, and placed on a microbe seeded culture plate according to the following standard culturing procedure:

Microbes were seeded onto a 5% sheep blood Mueller Hinton plate with an inoculum of $10^5$ CFU/ml and were placed at 35° C. for 18-24 hours incubation in an aerobic atmosphere (except for anaerobes). Zones of inhibition caused by the PVA/I complex were measured. Examples of wetting agents evaluated which are considered to be generally biocompatible were Tweens and Pleuronics. The controls contained no detergents.

| Organism | Zones of Inhibition in Millimeters Detergents | | | |
| --- | --- | --- | --- | --- |
| | Control # | Pleuronic F-68 | Tween 80 | Tween 20 |
| Pseudomonas cepacia | 38 | 68 | 46 | 50 |
| Bacillus SP | 17 | 58 | 20 | 20 |
| Pseudomonas aeruginosa | 12 | 28 | 12 | 40 |
| Staphylococcus aureus | 50 | 70 | 50 | ND |
| Escherichia coli | 40 | 72 | 71 | ND |

ND = (Not Done)

Surfactants generally increase antimicrobial activity and therefore allow faster kill, but to different degrees depending upon the microorganism. It may be possible to mix surfactants and concentrations to achieve a broader-spectrum activity, and dressings can be formulated for specific applications.

Increased Activity with Altered pH

In some instances, there may be a need for altering the pH of the PVA/I complex, as different organisms proliferate or are inhibited, depending on the acid or basic conditions of the environment. For example, in ear infections, the infecting organisms do not multiply at a pH of 4 or less. Therefore, incorporating acetic acid, boric acid, or other acid-producing compounds into the PVA/I complexed sponge is more effective than the iodine complex by itself, for this treatment.

Adhesive Dressings

There are many uses for dressings and antimicrobial draping systems that have self-adherent properties. A self-adhesive dressing with the brand name Band-Aid (Johnson & Johnson) is an example of such a product. A film drape to act as a sterile barrier during operations which has an antimicrobial adhesive coated on an inert film called Ioban2 (3M) is an example of an antimicrobial draping system.

There would be an advantage if the antimicrobial properties of the PVA/I complex could permeate through an adhesive layer so that dressings could be fabricated from PVA/I complex sponge tapes or film tapes whereby all parts of the dressing would be active and not just that portion which is not adhesive coated. Such microbiocidal tapes would also have the added advantages, for example, of providing an antimicrobial taping of wound site closures instead of using sutures or plain tape, and dressings that would have more long lived adherence and keep the wound site cleaner because of better sealing of the area around the wound from the environment. The advantages of an antimicrobial film that exerts its properties as well through the adhesive, as through the film, are that the skin and operative site are rendered more sterile, and the film acts as a barrier against contamination from the surrounding environment.

Ordinary, biocompatible adhesives commonly used to adhere drapes or dressings were used. These adhesives are often from the class of water-based acrylics. Hypoallergenic, pressure sensitive, acrylic transfer adhesives may be used.

The following experiment illustrates that PVA/I complex sheets, when adhesive coated to less than 1-2 mils, will exhibit similar antimicrobial properties, whether the adhesive side or non-adhesive side is in contact with the culture medium. If coatings thicker than 1-2 mils of adhesive are necessary, the adhesive may be printed on the PVA/I complex film or foam surface so that the adhesive is in discrete areas, allowing uncoated areas in intimate contact with the tissue. Lateral transfer of iodine into these adhesive covered areas, or absorption and antimicrobial action on serous fluids absorbed into the complexed absorptive medium will be affected by that portion of the iodine that still remains in the sponge and cannot permeate through the adhesive layer into the wound site.

V. Results of Testing Complexed PVA Systems

The following are the results of testing antimicrobial properties of complexed PVA systems:

PVA Film Systems

1. PVA post complexed with iodine.
2. PVA/aldehyde post complexed with iodine.
3. PVA/aldehyde post complexed with iodine and borate.
4. PVA post complexed with iodine and borate.
5. PVA post complexed with borate.

| Organism | Film System | Efficacy- Zone of Inhibition in MM |
| --- | --- | --- |
| Staphylococcus aureus | 1. | 4++ |
| | 2. | 4+ |
| | 3. | 4+ |
| | 4. | 4++ |
| | 5. | 0 |
| Candida albicans | 1. | 4+ |
| | 2. | 3+ |
| | 3. | 4+ |
| | 4. | 4+ |
| | 5. | 3+ |
| Pseudomonas aeruginosa | 1. | 3+ |
| | 2. | 0 to 1+ |
| | 3. | 2+ |
| | 4. | 3+ |
| | 5. | 0 |
| Interpretation of Efficacy | | |
| 0 | 0 MM | From the edge of Sample |
| 1+ | 2-4 MM | From the edge of Sample |
| 2+ | 5-7 MM | From the edge of Sample |
| 3+ | 8-12 MM | From the edge of Sample |
| 4+ | Over 12 MM | From the edge of Sample |
| 4++ | 20 MM | From the edge of Sample |

Conditions of test same as standard culturing procedures used in the activator experiments in $10^7$ CFU/ml 35° C. overnight incubation.

The results indicate the film can be as active as the foams in antimicrobial activity. The borate complex was particularly active against Candida albicans, and this demonstrated that antimicrobial effectiveness film can be custom-formulated in anticipation of use on sites likely to have certain known infections.

VI. Microbicidal Properties of High Density PVA/I Complexed Foam Containing Approximately 10% Iodine Based on Weight of Merodine Sponge.

Merodine ™ sponge is an experimental product which is expected to be manufactured and distributed by Americal Corp., the assignee of the present patent application. It is a derivative of Merocel ® sponge, which is manufactured by reacting an agent that kills micro-organisms with the Merocel polymer. The material in a dry state is stable at temperatures up to at least 125° F. Merodine sponge can be produced with different amounts of this agent to effect different potency levels.

The Merocel Sponge base is an open-celled hydroxylated polyvinyl acetal sponge. It has been used as the state-of-the-art surgical specialty sponge primarily due to its:

high absorbency,
non-linting characteristics,
biocompatibility,
strength,
abrasion resistance, and
softness of feel when moist.

Recent studies have shown that Merocel sponge by itself does not promote the growth of micro-organisms and particularly, that it does not amplify the production of the toxins associated with Toxic Shock Syndrome.

Merocel sponge is patented and is sanctioned by the F.D.A. for use in medical and health care fields.

Initial tests with the Merodine sponge showed that it has a remarkable ability to kill a wide variety of microorganisms including bacteria, fungi and viruses. Extensive studies on the comparative efficacy of the Merodine sponge against numerous microbes have confirmed this activity exemplified by the range of activity against the following organisms:

| Microbe (# strains)* | Degree of Inhibition** |
|---|---|
| *Escherichia coli* (8) | 4+ |
| *K. oxytoca* (2) | 4+ |
| *S. odorifera* (2) | 4+ |
| *Morganella morganii* (1) | 4+ |
| *Proteus vulgaris* (3) | 3-4+ |
| *Enterobacter cloacae* (2) | 4+ |
| *E. agglomerans* (1) | 4+ |
| *Kluyvera asorbata* (1) | 4+ |
| *Shigella sonnei* (1) | 4+ |
| *Citrobacter freundii* (1) | 4+ |
| *Ps. maltophilia* (1) | 3+ |
| *Acinetobacter anitratus* (1) | 4+ |
| *S. epidermidis* (1) | 4+ |
| *Streptococcus pneumoniae* (1) | 4+ |
| *St. agalactiae* (1) | 4+ |
| Corynebacterium sp (3) | 4+ |
| *Clostridium perfringens* (2) | 3-4+ |
| *Bacteroides fragilis* (1) | 4+ |
| *C. tropicalis* (1) | 3+ |
| *Torulopsis glabrata* (3) | 4+ |
| *Klebsiella pneumoniae* (3) | 4+ |
| *Serratia marcescens* (4) | 4+ |
| *S. rubideae* (1) | 4+ |
| Providencia sp (1) | 4+ |
| *Proteus mirabilis* (2) | 4+ |
| *E. aerogenes* (2) | 4+ |
| *E. sakazakii* (1) | 4+ |
| *Yersinia enterocolitica* (1) | 4+ |
| *Salmonella enteritidis* (1) | 4+ |
| *Pseudomonas aeruginosa* (4) | 2-4+ |
| *Ps. cepacia* (4) | 2-4+ |
| *Staphylococcus aureus* (1) | 4+ |
| *S. Saprophyticus* (1) | 4+ |
| *St. pyogenes* (Gp A) (2) | 4+ |
| Lactobacillus sp (2) | 4+ |
| Bacillus sp (2) | 3+ |
| *Cl. sordellii* (1) | 4+ |
| *Candida albicans* (3) | 3+ |
| *C. kreusii* (1) | 3+ |

| Interpretation of Efficacy | | |
|---|---|---|
| 0 | 0 MM | From the edge of Sample |
| 1+ | 2-4 MM | From the edge of Sample |
| 2+ | 5-7 MM | From the edge of Sample |
| 3+ | 8-12 MM | From the edge of Sample |
| 4+ | Over 12 MM | From the edge of Sample |
| 4++ | 20 MM | From the edge of Sample |

*Note: microbes were seeded onto a 5% sheep blood Mueller-Hinton plate with an inoculum of $10^5$ CFU/ml and were placed at 35° C. for 18-24 h incubation in an aerobic atmosphere (except for anaerobes). Zones of inhibition caused by the Merodine sponge were then measured.
**Range: 0 = none; 4+ = greatest.

As shown, it can be said that the Merodine sponge will kill and inhibit continued growth of almost any microorganism. In this sense, it is understood to be a unique material as these properties do not depend on introducing foreign bodies into the wound.

The speed and degree of kill can be controlled by:
varying the concentration of bactericidal agent;
changing the pore size and degree of porosity of the sponge substrate; or
incorporating activating agents. Testing is continuing on potency to determine:
how it is affected by the variables of ingredients and manufacturing methods; and
how quickly, and under what conditions it is dissipated during use.

Effect of Meordine Sponge on Healthy Tissue

Cytotoxicity tests are designed to show the possible effect that a material could have if it is placed in contact with healthy tissue. The tests are run on direct contact with the material and on contact with effluent from the material. The latter test simulates the possible effect of the material on tissue not in direct contact with it. The researcher looks for:

Cytopathic Effect—the material being tested changes the nature of the cells to giant cells or other abnormal forms of cells Cytocidal Effect—the material being tested kills cells that it contacts.

Merodine sponge was tested against Vero cells and Mink Lung cells.

Results show that the effluent from Merodine sponge does not alter or kill cells that it contacts (i.e. has no cytopathic or cytocidal effect). The sponge itself, in direct contact with a delicate monolayer of tissue, was not cytopathic or cytocidal to the cells it contacted. The killing of cells in direct contact could be expected, dependent upon the amount of iodine released. However, under test conditions none resulted with Merodine, most likely because of its controlled release of iodine.

Animal Experiments Include

1. Ocular Irritant
2. Skin Irritation
3. Surgical Pig Wound (Healing)
4. Muscle Implantation Study
5. TSS Animal Study These data indicate that Merodine sponge can be used safely for both medicinal purposes, such as wound dressings, as well as for general health care and hygiene, such as feminine tampons.

Further testing of the effect on healthy tissue is being conducted.

General Properties of Merodine Sponge

Merodine sponge is derived from a modification of the manufacturing process for Merocel sponge and could be produced in any form that can be cast, extruded, or cut from large blocks or from sheet material.

Merodine sponge can be laminated to other materials, including Merocel sponge.

In its dry state Merodine sponge is stiff and compressible. When placed in a humid or moist environment it becomes very soft and gentle to the touch.

Merodine sponge can be washed in water without dissipating its bactericidal properties.

Products Contemplated

The bactericidal properties of Merodine sponge suggest an extremely wide range of possible applications, both medical and consumer oriented.

It is dry, self-sterilizing material that is relatively innocuous to healthy tissue, but has the ability to kill most microbes.

It can be easily manufactured in many forms and packaged inexpensively.

The starting material, Merocel sponge, is itself highly biocompatible and does not promote the growth of micro-organisms, e.g. it does not amplify the production of the toxins associated with Toxic Shock Syndrome. These applications fall broadly into two categories:

Microbial control—killing of potentially infectious micro-organisms, e.g., wound dressings.

Odor control—killing of micro-organisms that produce odor, e.g., panty liners and foot odor control.

Products which would be used in direct contact with healthy tissue (e.g., feminine hygiene tampons) would be designed so that the Merodine sponge would not directly contact the tissue. Within these products, the function of the Merodine sponge would be to absorb body fluids and kill the micro-organisms without affecting the healthy tissue.

The following is a partial list of products that would benefit from the foregoing antimicrobial materials:

1. Clothing mildew protectors.
2. Drawer liners and shelf liners.
3. Closet liners to control fungi.
4. Tampons.
5. Panty liners.
6. Vaginal pads.
7. Perineal pads.
8. Surgical pads.
9. Surgical drapes
10. Diapers - baby.
11. Surgical instrument covers.
12. Surgical instrument protectors.
13. Surgical wipes.
14. Surgical instrument cleaners.
15. Adult incontinence pads.
16. Sanitizing and cleaning pads for household and industrial use.
17. Bandages, including sterile prepackaged plastic strip-type bandages, for example for household use.
18. Burn covers.
19. Wound covers.
20. Wound dressings.
21. Burn dressings.
22. Foot odor stoppers
23. Shoe liners insoles, midsoles.
24. Sneaker liners, insoles, midsoles.
25. Jogging shoe liners, insoles, midsoles.
26. Root canal tooth degerming agents (powder).
27. For use in ointment and other base skin treatments.
28. Acne pads.
29. Fruit wrappers and protectors.
30. Box or crate liners.
31. Women's dress underarm shields (odor control).
32. Men's suit underarm shields (odor control).
33. Army field bandages.
34. Decubitus ulcer dressings.
35. Decubitus ulcer cleaning wipes.
36. Wound cleaning wipes.
37. Debridement wipes
38. Contraceptive sponges.
39. Bone implants.
40. Surgical implants.
41. Toilet seat covers.
42. Waste paper baskets and liners.
43. Garbage pail liners.
44. Infectious material spill absorbers.
45. AIDS wipes.
46. AIDS virus contaminated spill absorbers
47. Sanitizing agents.
48. Sanitizing powders.
49. Hand sanitizing wipes.
50. First-Aid cleansers - germicide wipes.
51. Face sanitizing wipes.
52. Grain silo liners.
53. Computer box liners.
54. Electronic box liners.
55. Equipment box liners.
56. Liners for paper products.
57. Liners for film and photographic prints.
58. Vaginal anti-candida fungus pads.
59. Urine catheter bag inserts for controlling microbial growth and odor.
60. Human fluids aspirator device inserts for controlling microbial growth and odor.
61. Filters.
62. Water purifier devices.
63. Camea lens case liners.
64. Camera case liners.
65. Microscope lens case liners.
66. Optical lens case liners.
67. Animal cage floor liners.
68. Patient bed pads.
69. Leather briefcase liners and deodorizers.
70. Vinyl and other briefcase liners and deodorizers.
71. Sheet rock liners to prevent mold mildew buildup (helps allergic people in new house construction and home improvement).
72. Broadloom and carpet liners (to control buildup of bacteria and fungi) (also helps people with allergies).
73. Undersheets and liners for wood wall coverings to cut down or eliminate fungal mold growth.
74. Undersheets and coatings or roof in contact with wood to cut fungal mold growth.
75. Articulate with new lumber to cut mold growth in new construction and home improvements.
76. Undersheets and liners for "green boards" used in bathroom construction to cut growth of mold and mildew in damp areas.
77. Library and book shelving liners to reduce fungal mold growth.
78. Hemodialysis: filter blood prior to return to patient (good to prevent infection with small blood leaks in coil).
79. Filter blood from blood bank to make blood safe for use, re: AIDS, hepatitis, virus eradication.
80. Water-filtering systems using long filters with stopcocks, etc.
81. Final filter any body fluid prior to readministration to patient.
82. Colostomy site covers.
83. Operation site covers.

84. Round catheter covers.
85. Drainage site covers.
86. Arteriovenous shunt dressings and covers.
87. Shower floor mats.
88. Locker-room runners and mats.
89. Locker liners.
90. Laboratory bench work station covers.
91. Patient work station or procedure covers.
92. Blood filters.
93. Catheter coatings (to prevent UTI).
94. Laundry bags.
95. Continuous bandage strips.
96. Ear wick devices.
97. Antimicrobial preservative powders.
98. Litter box liners.
99. Litter boxes (also, addition of powder to litter material for odor control).
100. Pet baskets and beds (addition of powder for odor control).
101. Sterilizants and media for plant propogation.
102. Seedling protectors.
103. Plant root covers (prevents fungal destruction).
104. Plant protectors.
105. Plant covers (prevents fungal mold destruction).
106. Underliners for disposable baby blankets or wraps.
107. Crib mattress undercovers.
108. As powder component of face mask preps for treatment of skin conditions.
109. Urinal sterilizers (in men's rooms).
110. Underliners for carpeting etc. in automobiles, trucks, jeeps, buses and other vehicles.
111. Underliners for carpeting in airplanes or other airborne craft.
112. Underliners for carpeting etc. on seaborne and water borne craft.
113. Underliners for carpeting etc. on railroads and trains.
114. Ear cleaning swabs.
115. Navel (umbilicus) cleaning swabs.
116. Medicated ear stoppers for infected ears.
117. Medicated wound stoppers for other infected sites, e.g., catheters.
118. Tracheotomy opening covers.
119. Skull covers - post brain surgery.
120. Skull covers for Tinea Capitis (ringworm of head).
121. Nebulizer water reservoir bottom liners.
122. Humidifier water catch basin bottom liners.
123. Shower and bathtub degerming cleaners (sanitize wipes).
124. Plant graft wraps and protectors.
125. NASA - space bandages.
126. NASA - Spacecraft sanitized wipes.
127. NASA - Spacecraft capsule liners, components, etc.
128. NASA - Space station liners (interior).
129. NASA - Astronaut suit liners to control growth.
130. Burn blankets coated with iodine gel.
131. Antimicrobial tape closures instead of sutures.

Although the present invention has been described in relation to a particular embodiment thereof, many other variations and other uses will become apparent to those skilled in the art. It is preferred, therefore, that the Although the present invention has been described in relation to a particular embodiment thereof, many other variations and other uses will become apparent to those skilled in the art. It is preferred, therefore, that the present invention be limited not by the specific disclosure herein, but only by the appended claims.

What is claimed is:

1. A composition comprising acetalized polyvinyl alcohol complexed with iodine, wherein said composition is capable of releasing free iodine in the presence of water.

2. The composition of claim 1 wherein said acetalized polyvinyl alcohol is a hydroxylated polyvinyl acetal sponge.

3. The composition of claim 1 wherein said acetalized polyvinyl alcohol is further complexed with a borate.

4. The composition of claim 1 wherein said composition is a sponge, foam or gel.

5. An antimicrobial product which includes a composition comprising acetalized polyvinyl alcohol complexed with iodine, wherein said composition is capable of releasing free iodine ions in the presence of water.

6. The product of claim 5 wherein said product further comprises a substrate for receiving said film, said substrate being selected from the group consisting of cloth or nonwoven webbing.

7. The product of claim 6 wherein said product is selected from the group consisting of filters, wound dressings, topical pads, cleansing wipes and odor control shields.

8. A method of controlling infection, said method comprising topical application of a product which includes an antimicrobially effective amount of a controlled-release agent, said agent comprising iodine in complex with a polymer selected from the group consisting of polyvinyl alcohol and acetalized polyvinyl alcohol, and said controlled release agent being capable, in the presence of water, of releasing free iodine.

9. The method of claim 8 wherein said product is a wound dressing.

10. The method of claim 9 wherein said wound dressing changes color as iodine in said controlled release agent is depleted.

11. The method of claim 8 wherein said polymer is further complexed with a borate.

* * * * *